(12) United States Patent
Merritt et al.

(10) Patent No.: US 7,799,367 B2
(45) Date of Patent: Sep. 21, 2010

(54) SYSTEMS AND METHODS FOR COATING CATHETER SHAFTS

(75) Inventors: Ryan P. Merritt, Boca Raton, FL (US); Dina E. Agrapides, South Bound Brook, NJ (US); Vicente J. Fuillerat, Lakeland, FL (US)

(73) Assignee: Cordis Corporation, Miami Lakes, FL (US)

( * ) Notice: Subject to any disclaimer, the term of this patent is extended or adjusted under 35 U.S.C. 154(b) by 950 days.

(21) Appl. No.: 11/580,462

(22) Filed: Oct. 13, 2006

(65) Prior Publication Data
US 2008/0171130 A1 Jul. 17, 2008

(51) Int. Cl.
*A61L 33/00* (2006.01)

(52) U.S. Cl. .................... 427/2.24; 427/2.12; 427/2.25; 427/2.3; 427/430.1

(58) Field of Classification Search ............... 427/2.24, 427/430.1, 2.3; 118/416, 423, 428
See application file for complete search history.

(56) References Cited

U.S. PATENT DOCUMENTS

| | | | |
|---|---|---|---|
| 5,041,100 A | 8/1991 | Rowland et al. | |
| 5,053,048 A | 10/1991 | Pinchuk | |
| 5,370,615 A | 12/1994 | Johnson | |
| 5,788,681 A | 8/1998 | Weaver et al. | |
| 5,820,594 A | 10/1998 | Fontirroche | |
| 6,364,894 B1 | 4/2002 | Healy | |
| 6,461,644 B1 | 10/2002 | Jackson et al. | |
| 6,663,648 B1 | 12/2003 | Trotta | |
| 6,919,100 B2 | 7/2005 | Narayanan | |
| 2003/0135195 A1 | 7/2003 | Jimenez et al. | |

OTHER PUBLICATIONS

DipTech Systems Inc., Catheter Dipping and Coating Line, 2004, www.diptechsystems.com/photos.htm, pp. 1 and 2.*

* cited by examiner

*Primary Examiner*—Michael Barr
*Assistant Examiner*—Andrew Bowman

(57) ABSTRACT

Medical catheters are often coated, fully or partially. The present invention relates to systems and methods for coating some portion or all of a medical catheter or one or more of its components.

8 Claims, 2 Drawing Sheets

SYSTEMS AND METHODS FOR COATING CATHETER SHAFTS

BACKGROUND AND SUMMARY OF THE INVENTION

1. Technical Background

The present invention relates generally to medical devices, and more particularly to applying coatings to catheter shafts.

2. Discussion

Catheters are used in a variety of therapeutic applications, and are available in a variety of types including diagnostic catheters, guiding catheters, balloon catheters, catheter sheath introducers, etc. The present invention relates to systems and methods for applying a coating to one or more catheter shaft components.

By way of example, the present invention will be described in relation to balloon catheters, diagnostic catheters, and guiding catheters. However, it should be understood that the present invention relates to any system or method of coating all or part of one or more medical catheter components, according to the present invention as recited in the following claims, and it is not otherwise limited to angioplasty, or balloon catheters, or any other feature that may be described in this description.

Structurally, many balloon catheters have a relatively long and flexible tubular shaft defining one or more passages or lumens, and an inflatable balloon attached near one end of the shaft.

The end of the catheter where the balloon is located is customarily referred to as the "distal" end, while the other end is called the "proximal" end. The proximal end of the shaft is generally coupled to a proximal hub.

In greater detail, the hub defines a proximal inflation port, and may define a proximal guidewire port. The proximal inflation port communicates with an inflation lumen defined by the shaft, which extends and is connected to the interior of the balloon, for selectively inflating and deflating the balloon.

If the balloon catheter has a guidewire lumen for slidingly receiving a guidewire, the guidewire lumen will extend between a proximal guidewire port, and a distal guidewire port located at the distal end of the catheter. If the proximal guidewire port is defined at the hub, the resulting arrangement is referred to as "over-the-wire." And if the proximal guidewire port is located at some intermediate point along the shaft, the resulting configuration is called "rapid-exchange."

Examples of balloon catheters are shown in the following United States patents, all of which are commonly owned with the present invention: (i) U.S. Pat. No. 6,663,648, entitled "Balloon catheter with floating stiffener, and procedure," issued to Trotta on Dec. 16, 2003; (ii) U.S. Pat. No. 6,364,894, entitled "Method Of Making An Angioplasty Balloon Catheter," issued to Healy et al. on Apr. 2, 2002; (iii) U.S. Pat. No. 5,820,594, entitled "Balloon Catheter," issued to Fontirroche et al. on Oct. 13, 1998; and (iv) U.S. Pat. No. 5,370,615, entitled "Balloon Catheter For Angioplasty," issued to Johnson on Dec. 6, 1994.

Structurally, diagnostic catheters also have a proximal hub affixed to a tubular flexible catheter shaft. Some reinforcement, such as metal wire braid, may be provided in the sidewall of the tubular shaft. In general, diagnostic catheters do not have a balloon.

Similarly, guiding catheters also have a proximal hub affixed to a tubular flexible catheter shaft, which is larger in diameter or lumen size than comparable balloon or diagnostic catheters. Guiding catheters in particular may have a distal tip of a radiopaque material which is visible on an x-ray fluoroscope.

It may be desirable to apply a coating to a portion or all of the shaft component(s) of a catheter. For example, a lubricious coating can reduce friction along portions of the catheter shaft. One particular type of lubricious coating is hydrophilic coatings, which become slippery on contact with water or other liquids.

However, a characteristic of lubricious coatings is of course that they are slippery, and it may be desirable to specifically avoid coating some portions of the catheter. For example, it may be preferred that the catheter shaft proximal end have no coating, so the proximal hub can be securely affixed to the shaft. Another example is that it may be preferred not to apply the coating to a distal end of the catheter shaft. For example, if a balloon will be affixed to the catheter shaft distal end, or if other medical devices such as a stent will be provided, then that portion of the shaft should not have a lubricious coating.

Different types of coating may be applied using the systems and methods of the present invention, including for example anticoagulant coatings or therapeutic coatings such as drug-eluting coatings.

It may be desirable to apply a coating only to a portion of a catheter shaft component, or perhaps only an intermediate portion between that component's proximal and distal ends. In addition, it may be desirable to apply such a partial coating without using a mask or similar techniques and methods.

Likewise, it may also be desirable to provide for an efficient, repeatable and scaleable coating process, as well as a coating process that provides even coating density. Another possibly desirable feature is to provide for evenly drying or curing the coating, without allowing the initial fluid coating to run down and gather at one portion of the shaft component. For example, it is desirable to avoid any droplets of coating materials, or other coating inconsistencies.

It may also be desirable to coat only an intermediate portion of a catheter shaft component, without coating the proximal and distal ends or portions of the catheter shaft component, and also with the even coating aspects mentioned above.

Also, it may be desirable in the case of tubular catheter components defining at least one lumen, to avoid allowing any coating materials to enter inside a lumen.

In addition, it may be desirable to provide coating systems and methods to improve product yield rates during manufacturing.

These and various other objects, advantages and features of the invention will become apparent from the following description and claims, when considered in conjunction with the appended drawings. The invention will be explained in greater detail below with reference to the attached drawings of a number of examples of embodiments of the present invention.

DETAILED DESCRIPTION OF THE PREFERRED EMBODIMENTS

The following description of the preferred embodiments of the present invention is merely illustrative in nature, and as such it does not limit in any way the present invention, its application, or uses. Numerous modifications may be made by those skilled in the art without departing from the true spirit and scope of the invention.

According to one example of the present invention, the drawings show a system for coating catheter shaft components.

A tank 10 holds a fluid 12 which defines a fluid level 14, which is the coating material in fluid form.

For illustration purposes, an example catheter shaft component 16 is shown, having a first and second end.

Figure 1:
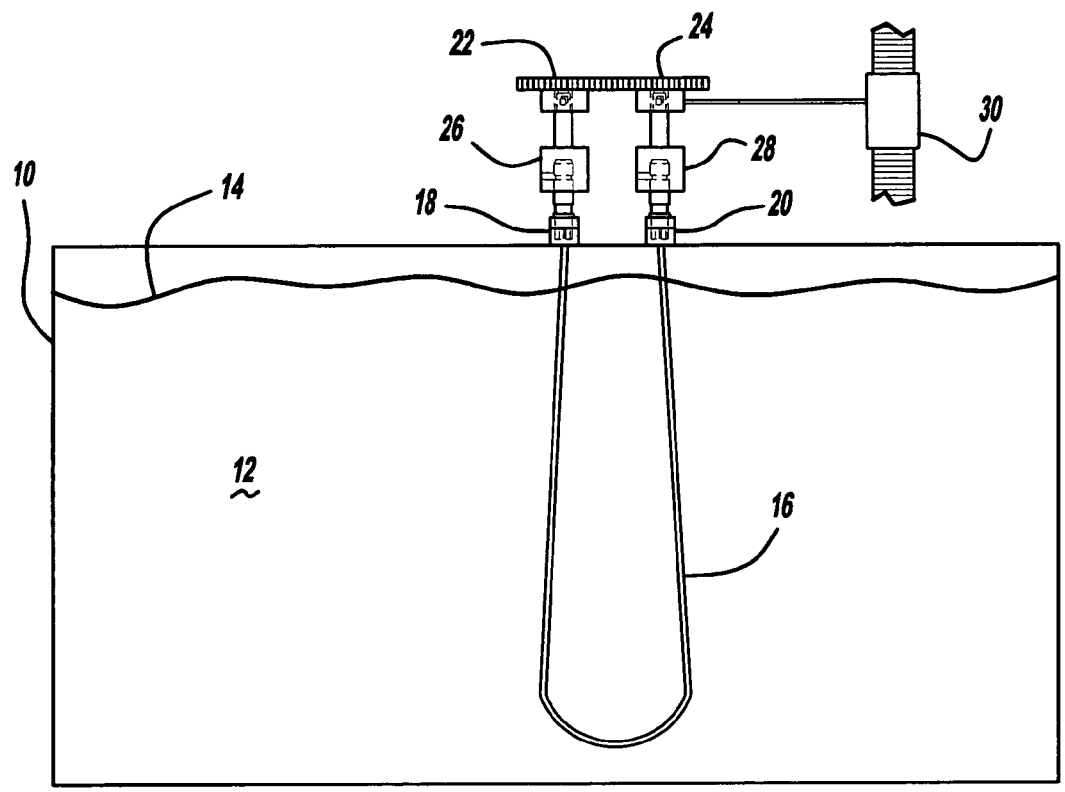
FIG. 1 is a side elevation view of a partially diagrammatic example of a system for coating catheter components.

The system includes a first and second clasp 18 and 20, which are shown in FIG. 1 clasping the first and second end of the catheter shaft component 16, respectively. A first and second gear 22 and 24 is coupled with the first and second clasp 18 and 20, respectively, and the gears 22 and 24 are meshed to limit rotation of the first and second clasp 18 and 20 to equal and opposite directions.

The clasps 18 and 20 are relatively close together, at a distance much shorter than a length of the catheter shaft component 16, so that it hangs down from the clasps in a "U" shape.

An actuator 26 and 28 such as for example an electric motor or servo is coupled with each of the clasps 18 and 20, to selectively rotate the catheter shaft component around its longitudinal axis.

A mechanism 30 is shown in a diagrammatic fashion, which can selectively raise and lower the assembly of the clasps, gears, and catheter shaft component. The mechanism 30 can thus raise and lower the catheter shaft component 16 down into and up out of the fluid 12. When the assembly has been raised, the catheter shaft component 16 may be moved to a separate location for drying or curing the coating on the catheter shaft component, or the coating may be dried or cured directly above the fluid tank.

During drying or curing of the coating, the actuators 26 and 28 may continue to rotate the catheter shaft component 16 about its longitudinal axis. This rotation during cure will tend to prevent formation of a hardened droplet of coating material at the bottom of the "U"-shaped catheter shaft component.

In detail, FIG. 1 shows a catheter shaft component 16 having a first and second end held by a first and second clasp 18 and 20, which can be rotated by a first and second actuator 26 and 28, which are limited by a first and second gear 22 and 24 to rotate the clasps 18 and 20 in equal and opposite directions.

Figure 2:
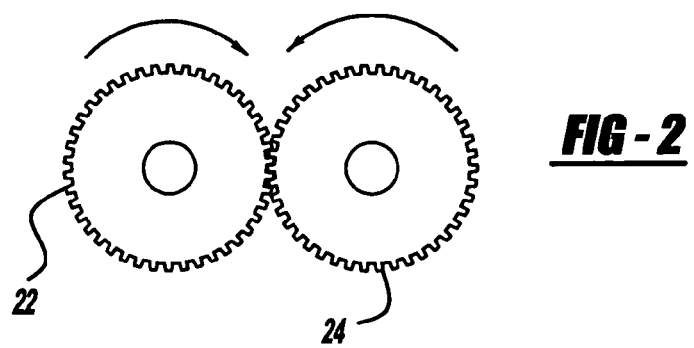
FIG. 2 is a top view of counter-rotating gears for a system for coating catheter components.

FIG. 2 shows a top view of the first and second gear 22 and 24, which counter-rotate in the directions of the arrows, or in equal and opposite directions.

Figure 3:
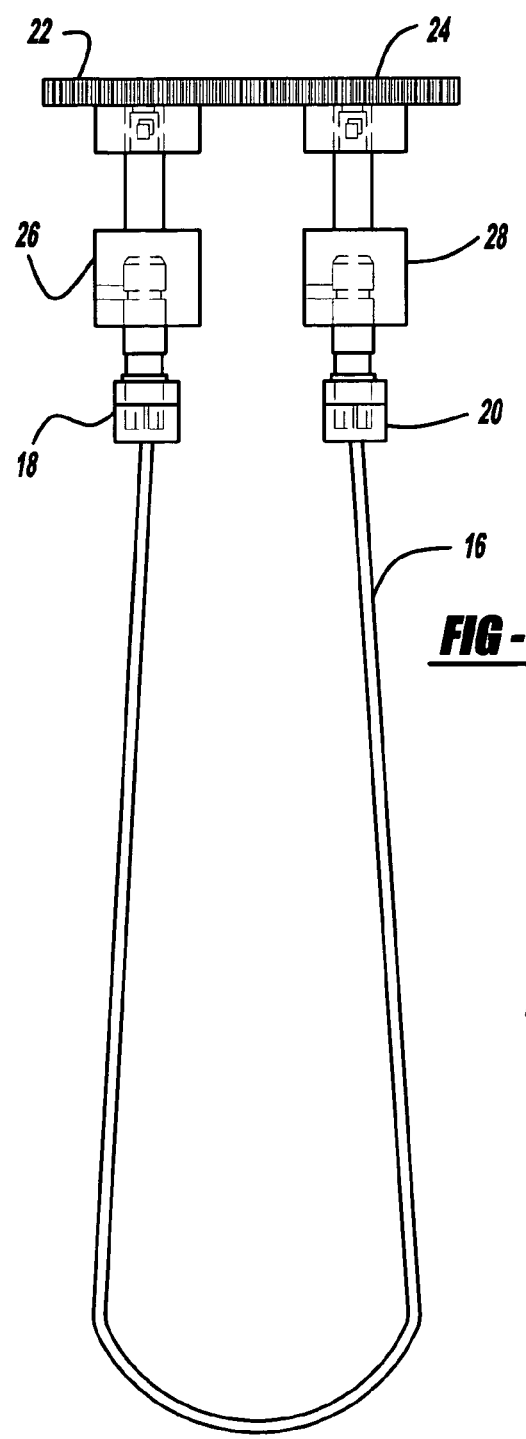
FIG. 3 is a side elevation view of a system for drying or curing a coating on a catheter component.

FIG. 3 shows the catheter shaft component 16, clasps 18 and 20, actuators 26 and 28, and gears 22 and 24 in a drying or curing position.

Figure 4:
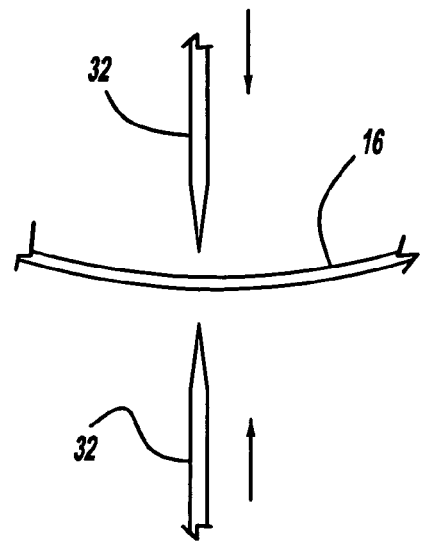
FIG. 4 is a partially diagrammatic view of a portion of a catheter component and a pair of cutting blades.

FIG. 4 shows a catheter shaft component 16 and an example of an optional pair of cutting blades 32, for use in the event that it is desirable to have the coating extend to each of the newly formed ends which will result from using the cutting blades 32.

It should be understood that an unlimited number of configuration for the present invention could be realized. The foregoing discussion describes merely exemplary embodiments illustrating the principles of the present invention, the scope of which is recited in the following claims. Those skilled in the art will readily recognize from the description, claims and drawings that numerous changes and modifications can be made without departing from the spirit and scope of the invention.

What is claimed is:

1. A method of coating a catheter component, comprising the steps of:
   (a) providing a catheter component defining a length and a longitudinal axis, and having a first and second end; providing a container and a fluid in the container; the fluid being one or more coating materials in fluid form and defining a fluid level; providing a first and second clasp for releasably holding the first and second end of the catheter component, respectively; providing an actuator for selectively rotating the first clasp to selectively rotate the catheter component around its longitudinal axis; wherein the clasps and actuator define an assembly; and providing a mechanism for selectively raising and lowering the assembly;
   (b) clasping the first and second ends of the catheter component with the clasps, and positioning the clasps relatively close together, at a distance substantially less than the catheter component length, such that the catheter component tends to hang down from the clasps in a "U" shape;
   (c) the mechanism lowering the catheter component into the fluid until the fluid level reaches a position on the catheter component; the actuator rotating the catheter component in the fluid;
   (d) following a selected elapsed time, the mechanism raising the catheter component from the fluid and holding the catheter component in a curing position; the actuator rotating the catheter component in the curing position; such that the fluid forms a coating on the catheter component; and
   (e) releasing the clasps and removing the coated catheter component from the assembly.

2. The method of claim 1, further comprising a second actuator;
   wherein during said rotating steps, the second actuator rotates the catheter component second end in an equal and opposite direction to the first actuator.

3. The method of claim 1, further comprising a second actuator, and further comprising a mechanism for limiting rotation of the first and second actuators to equal and opposite directions;
   wherein during said rotating steps, the second actuator rotates the catheter component second end in an equal and opposite direction to the first actuator.

4. The method of claim 3, wherein the rotation limiting mechanism is a pair of gears in mutual engagement.

5. The method of claim 1, wherein the fluid is hydrophilic, and forms a hydrophilic coating on the catheter component.

6. The method of claim 1, wherein the catheter component is tubular and defines a lumen, and wherein the clasps define seals to resist entry of the fluid in the tank into the lumen of the catheter component.

7. The method of claim 6, wherein said step (a) further comprises providing a cutter; and further comprising, between steps (d) and (e), the additional step of:
   cutting the catheter component, forming a first and second resulting catheter component, each with a coating extending to one end thereof.

8. The method of claim 7, wherein each lumen defined by the first and second resulting catheter component is substantially free of coating.

* * * * *